(12) United States Patent
Simske et al.

(10) Patent No.: US 10,394,867 B2
(45) Date of Patent: Aug. 27, 2019

(54) FUNCTIONAL SUMMARIZATION OF NON-TEXTUAL CONTENT BASED ON A META-ALGORITHMIC PATTERN

(71) Applicant: Hewlett-Packard Development Company, L.P., Spring, TX (US)

(72) Inventors: Steven J Simske, Ft. Collins, CO (US); A. Marie Vans, Ft. Collins, CO (US); Malgorzata M Sturgill, Ft. Collins, CO (US); Julie e Hurley, Chicago, IL (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 267 days.

(21) Appl. No.: 15/317,940

(22) PCT Filed: Jun. 11, 2014

(86) PCT No.: PCT/US2014/041907
§ 371 (c)(1),
(2) Date: Dec. 11, 2016

(87) PCT Pub. No.: WO2015/191061
PCT Pub. Date: Dec. 17, 2015

(65) Prior Publication Data
US 2017/0132319 A1 May 11, 2017

(51) Int. Cl.
*G06F 17/30* (2006.01)
*G06F 16/34* (2019.01)
(Continued)

(52) U.S. Cl.
CPC .......... *G06F 16/345* (2019.01); *G06F 16/353* (2019.01); *G06F 16/907* (2019.01);
(Continued)

(58) Field of Classification Search
CPC ......... G06F 17/30719; G06F 17/30017; G06F 17/30843; G06F 17/212; G06F 17/30699; G06F 17/30743
(Continued)

(56) References Cited

U.S. PATENT DOCUMENTS

| 5,864,630 A | 1/1999 | Cosatto et al. |
| 7,406,453 B2 | 7/2008 | Mundie et al. |

(Continued)

OTHER PUBLICATIONS

Ding, J, "Improving Text Clustering for Functional Analysis of Genes", 2006.
(Continued)

*Primary Examiner* — Dangelino N Gortayo
(74) *Attorney, Agent, or Firm* — HP Inc. Patent Department (57) ABSTRACT

Functional summarization of non-textual content based on a meta-algorithmic pattern is disclosed. One example is a system including a converter, a plurality of summarization engines and/or meta-algorithmic patterns, an extractor, and an evaluator. The converter converts the non-textual content into a plurality of tokens. Combinations of summarization engines and/or meta-algorithm patterns are applied to the plurality of tokens to provide a meta-summary. The extractor extracts at least one summarization term from the meta-summary, and at least one class term for each given class of a plurality of classes of non-textual content. The evaluator determines similarity values of the non-textual content over each given class, each similarity value indicative of a similarity between the at least one summarization term and the at least one class term for each given class. The selector selects a class of the plurality of classes, the selecting based on the determined similarity values.

8 Claims, 5 Drawing Sheets

(51) Int. Cl.
*G06F 16/35* (2019.01)
*G06F 17/27* (2006.01)
*G06F 16/907* (2019.01)
*G16H 50/70* (2018.01)
*G06F 16/335* (2019.01)
*G06F 16/683* (2019.01)
*G06F 16/2457* (2019.01)

(52) U.S. Cl.
CPC ...... *G06F 17/277* (2013.01); *G06F 16/24578* (2019.01); *G06F 16/335* (2019.01); *G06F 16/683* (2019.01); *G06F 17/2725* (2013.01); *G16H 50/70* (2018.01)

(58) Field of Classification Search
USPC .................. 707/737, 748, 736, 738, 722
See application file for complete search history.

(56) References Cited

U.S. PATENT DOCUMENTS

| | | | | |
|---|---|---|---|---|
| 8,392,183 | B2* | 3/2013 | Weber | G11B 27/28 700/94 |
| 8,463,756 | B2* | 6/2013 | Sarshar | G06F 17/30784 707/690 |
| 8,489,600 | B2* | 7/2013 | Hannuksela | G06F 17/3002 707/736 |
| 8,607,332 | B2 | 12/2013 | Canard et al. | |
| 2002/0046018 | A1 | 4/2002 | Marcu et al. | |
| 2004/0236805 | A1* | 11/2004 | Gordon | G06F 17/30719 |
| 2005/0123053 | A1 | 6/2005 | Cooper et al. | |
| 2005/0203970 | A1* | 9/2005 | McKeown | G06Q 10/10 |
| 2008/0109425 | A1 | 5/2008 | Yih et al. | |
| 2008/0300872 | A1 | 12/2008 | Basu et al. | |
| 2009/0006082 | A1 | 1/2009 | Harris | |
| 2010/0031142 | A1 | 2/2010 | Nagatomo | |
| 2012/0278300 | A1* | 11/2012 | Soubbotin | G06F 16/338 707/706 |
| 2013/0262146 | A1 | 10/2013 | Price | |
| 2014/0100885 | A1* | 4/2014 | Stern | G06Q 10/10 705/3 |
| 2014/0222834 | A1* | 8/2014 | Parikh | G06F 17/30867 707/748 |
| 2015/0154236 | A1* | 6/2015 | Aravkin | G06F 17/30321 707/737 |

OTHER PUBLICATIONS

Popescu, M et al, "Functional Summarization of Gene Product Clusters Using Gene Ontology Similarity Measures", Dec. 14-17, 2004.

* cited by examiner

FUNCTIONAL SUMMARIZATION OF NON-TEXTUAL CONTENT BASED ON A META-ALGORITHMIC PATTERN

BACKGROUND

Summarizers are computer-based applications that provide a summary of some type of content. Meta-algorithms are computer-based applications that can be applied to combine two or more summarizers, analysis algorithms, systems, or engines to yield meta-summaries. Meta-summaries may be used in a variety of applications, including non-text analytics.

DETAILED DESCRIPTION

Functional summarization of non-textual content based on a meta-algorithmic pattern is disclosed. The non-textual content may include, for example, an image, audio content, video content, binary data, genetic data, and healthcare data, among others. The functional summarization involves generating intelligence from content and may be used as a decision criterion for non-textual analytics.

As described in various examples herein, functional summarization is performed with combinations of summarization engines and/or meta-algorithmic patterns. A summarization engine is a computer-based application that receives a text document and provides a summary of the text document. A meta-algorithmic pattern is a computer-based application that can be applied to combine two or more summarizers, analysis algorithms, systems, and/or engines to yield meta-summaries, in one example, multiple meta-algorithmic patterns may be applied to combine multiple summarization engines.

A non-textual document may be converted into a plurality of tokens. Such tokenized non-textual content may be treated as a textual language, and functional summarization may be performed in a manner similar to summarization of a text document. More particularly, a vocabulary of tokens for the non-textual content substitutes for a vocabulary of words in text processing. Accordingly, a plurality of combinations of summarization engines and/or meta-algorithmic patterns may be applied to the tokenized non-textual content to generate a meta-summary.

The output of the meta-algorithmic pattern may be used as input in the same way as the output of individual summarization engines) for classification of the non-textual content into a plurality of classes. Each class may include non-textual content, including images, audio, video, binary data, genetic data, healthcare data, and so forth. Summarization terms may be extracted from meta-summary, where the summarization terms include key tokens that are representative of the meta-summary. Class terms representative of a given class of non-textual content may be generated from the non-textual content in each class. The summarization terms may be compared to the class terms for each class to determine similarity values of the non-textual content over each class. A class, of the plurality of classes may be selected based on the similarity values, and the non-textual content may be associated with the selected class.

As described herein, meta-algorithmic patterns are themselves pattern-defined combinations of two or more summarization engines, analysis algorithms, systems, or engines; accordingly, they are generally robust to new samples and are able to find a classification of non-textual content based on a ranking of the classes. Such ranking of the classes may be based, for example, on the determined similarity values.

In the following detailed description, reference is made to the accompanying drawings which form a part hereof and in which is shown by way of illustration specific examples in which the disclosure may be practiced. It is to be understood that other examples may be utilized, and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

Figure 1:
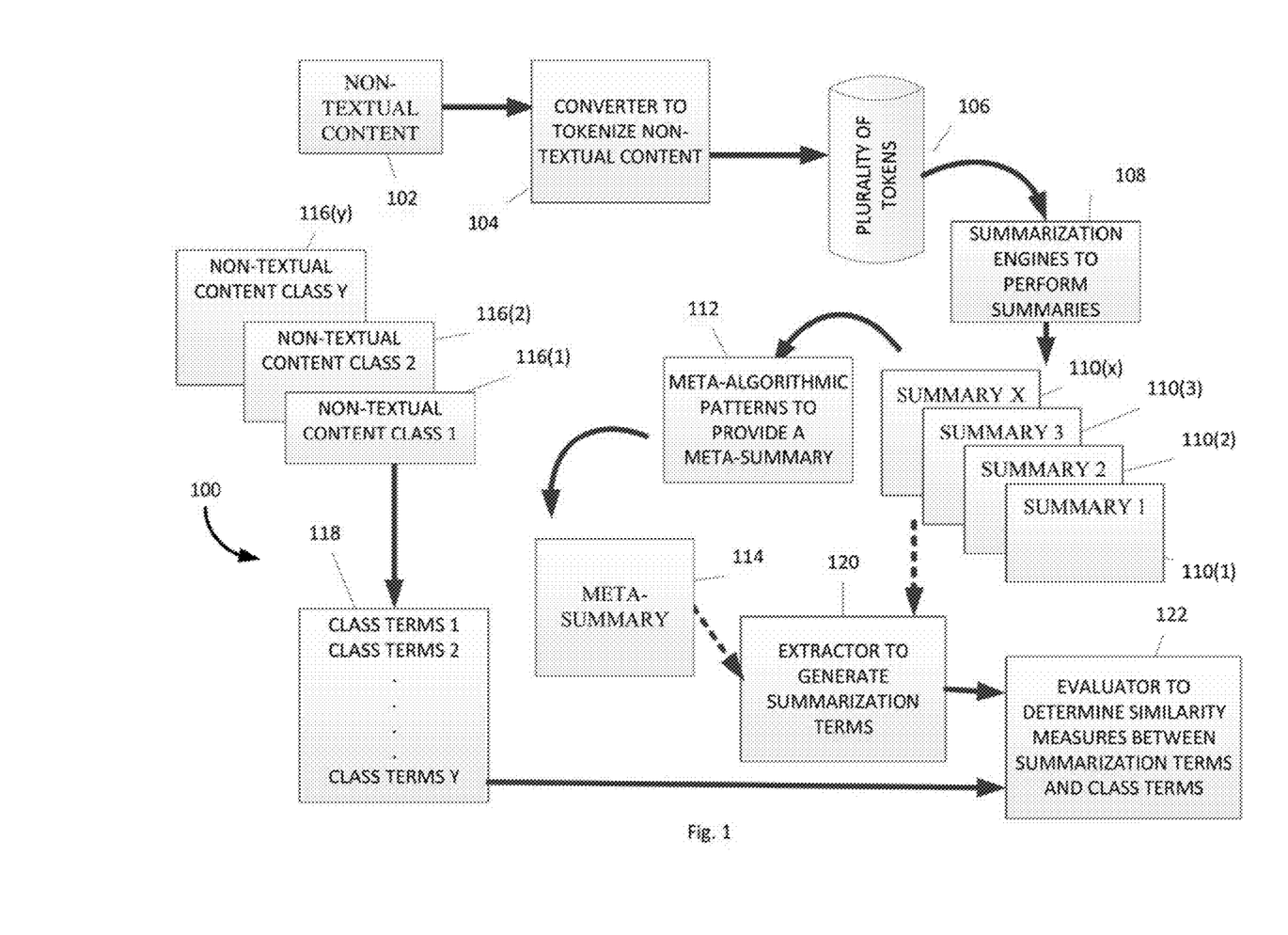
FIG. 1 is a functional block diagram illustrating one example of a system for functional summarization of non-textual content based on a meta-algorithmic pattern.

FIG. 1 is a functional block diagram illustrating one example of a system 100 for functional summarization of non-textual content based on a meta-algorithmic pattern. The system receives non-textual content, such as an image, audio and/or video content, and converts the non-textual content into a plurality of tokens. The plurality of tokens is then processed by a plurality of different summarization engines to provide a plurality of summaries. The summaries may be further processed by at least one meta-algorithmic pattern, each meta-algorithmic pattern to be applied to at least two summaries, to provide a meta-summary, where the meta-summary is provided using the at least two summaries. System 100 may treat the meta-summary as a new summary. For example, the meta-summary may be utilized as input for classification in the same way as an output from a summarization engine. As another example, the meta-summary may be utilized as input for determining search behavior in the same way as an output from a summarization engine.

The system 100 also identifies at least one class term for each given class of a plurality of classes of non-textual content, the at least one class term extracted from non-textual content in the given class. In one example, a class vector may be generated for each given class of a plurality of classes of non-textual content, the class vector being based on the at least one class term for each given class. The system 100 also extracts at least one summarization term from the meta-summary. In one example, a summarization vector may be generated, the summarization vector being based on the at least one summarization term extracted from the meta-summary.

Similarity values of the non-textual content over each class of documents of the plurality of classes of non-textual content are determined, each similarity value indicative of a similarity between the at least one summarization term and the at least one class term for each given class. In one example, the similarity values may be determined as a cosine similarity between the summarization vector and each class vector. A class of the plurality of classes may be selected, the selection based on the determined similarity values. The non-textual content may be associated with the selected class of non-textual content. In one example, each summary and/or meta-summary may be associated with a distinct weight determination for each class of non-textual content. An Output Probabilities Matrix may be generated based on such weight determinations, and the classification of the non-textual content may be based on the Output Probabilities Matrix. In one example, the non-textual content may be associated with a class that has an optimal weight determination.

Meta-summaries are summarizations created by the intelligent combination of two or more standard or primary summaries. The intelligent combination of multiple intelligent algorithms, systems, or engines is termed "meta-algorithmics", and first-order second-order, and third-order patterns for meta-algorithmics may be defined.

System 100 includes non-textual content 102, a converter 104, a plurality of tokens 106, summarization engines 108, summaries 110(1)-110($x$), at least one meta-algorithmic pattern 112, a meta-summary 114, an extractor 120, a plurality of classes of non-textual content 116(1)-116($y$), class terms 118 for each given class of the plurality of classes of non-textual content, and an evaluator 122, where "x" is any suitable numbers of summaries and "y" is any suitable numbers of classes and class terms. Non-textual content 102 may include an image, audio and/or video content, binary data, genetic data, and/or healthcare data. Video content may include one video, portions of a video, a plurality of videos, and so forth. Likewise, genetic data may include genetic data from an individual, a group of individuals, portions of genetic data, genetic data of one or several organisms, and so forth. Binary data includes any data that may be represented by a sequence of 0's and 1's.

Converter 104 converts non-textual content 102 to provide a plurality of tokens 106 suitable for processing by summarization engines 108. In one example, converter 104 converts video content into a set of descriptors. These descriptors of the video content may comprise a vocabulary which can be very concrete, as is the case for a dictionary of segmented object types. In one example, the descriptors of the video content may be abstract, as in visual descriptors, including shape, color, texture, bounding boxes (e.g., regions), motion, and so forth.

In one example, converter 104 tokenizes binary data to create a vocabulary based on salient binary substrings. In one example, converter 104 may identify key functional sets from binary data, such as, for example, randomness of the binary data. For example, bit stream entropy, statistics on uniqueness collisions encountered during mass serialization database collection, and differential byte statistics to test for reduced entropy (indicative of cryptographic threats) may be utilized to tokenize binary data. Functional summarizations may be performed on such tokenized data.

In one example, converter 104 converts genetic data into binary data for the purposes of functional summarization. Genetic data may be utilized to identify patients without surrendering potentially compromising clinical and/or prognostic information. In the case of genetic information, a patient's DNA is assigned to two logical sequences, the introns, which are associated with the transcription of genes, and the exons, which are DNA sequences not directly associated with genes. The exons may not be associated with an individual's risk for genetically-associated disease. Accordingly the exons may be summarized to form a look-up for patient participation in clinical trials and for other situations in which a dual-access security/privacy mechanism may be preferable. Generally, the axons may be treated as quaternary sequences (pairs of bits) where for example adenosine is "00", cytosine is "01", guanine is "10", and thymine is "11". A similar mapping may be used for RNA, protein sequences, and so forth. Once genetic data is converted into binary data, functional summarization of genetic data may proceed as for binary data. In one example, converter 104 converts healthcare data into binary data. Publicly available healthcare data may be converted to genetic and/or binary data.

In one example, a filter may remove blank sections, text, and/or other portions of non-textual content 102. In one example, converter 104 may perform the functions of the filter.

Summarization engines 108 summarize the plurality of tokens 106 to provide a plurality of summaries 110(1)-110($x$). In one example, the non-textual content 102 may be video content including a plurality of videos, and the plurality of tokens 106 may include descriptors for each of the plurality of videos. In one example, each of the summarization engines provides a summary of the non-textual content, including one or more of the following summarization outputs:

(1) a set of key images;
(2) a set of key audio;
(3) an extractive set of tokens;
(4) an extractive set of video clips;
(5) an extractive set of clustered binary strings, and other non-textual chunks; or
(6) an abstractive, or semantic, summarization of the tokenized non-textual content.

In other examples, a summarization engine may provide a summary including another suitable summarization output. Different statistical language processing ("SLP") and natural language processing ("NLP") techniques may be used to generate the summaries. For example, a textual transcript of a video may be utilized to provide a summary. In one example, portions of the video may be extracted based on the summary.

In one example, the non-textual content 102 may be video content, and the image set, comprising the video content, may be associated with descriptors to form a vocabulary. The summarization engines may then provide summaries based on such a vocabulary. In one example, the plurality of tokens 106 (or descriptors) may be treated as a textual language, and functional summarization may be performed in a manner similar to summarization of tokenized non-textual content, where in this case the vocabulary of tokens effectively substitutes for a vocabulary of words in text processing.

In one example, the non-textual content 102 may be binary data. As described herein, a plurality of tokens 106 may be generated from the binary data based on salient binary substrings that occur in the binary data. Randomness of data is another key feature of binary data, and summarization may include identifying patterns that are representative of the randomness of the binary data. For example, a summary may include a substring with a high frequency in the binary data.

Figure 2:
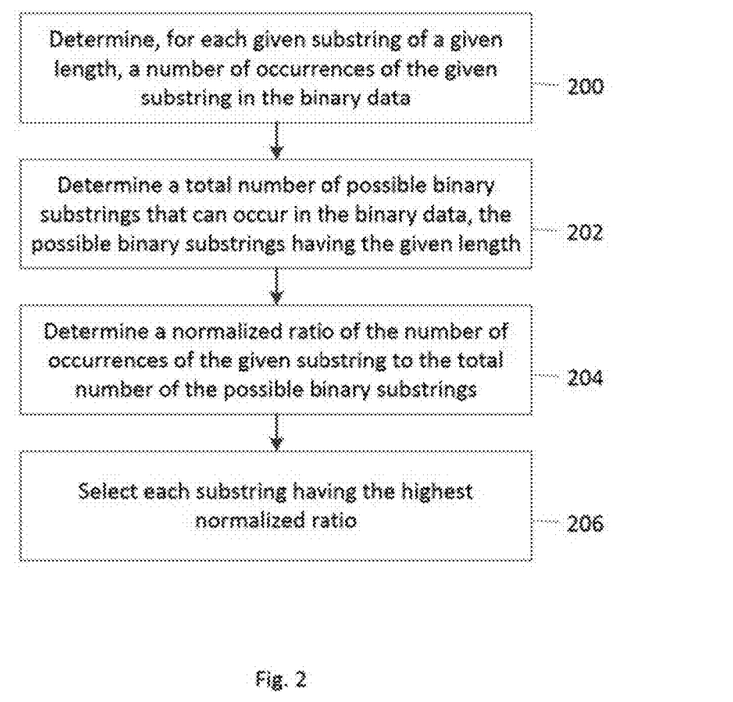
FIG. 2 is a flow diagram illustrating one example of a method for determining a substring of high frequency in binary data.

FIG. 2 is a flow diagram illustrating one example of a method for determining a substring of high frequency in binary data. At 200, for each given substring of a given length, a number of occurrences of the given substring in the binary data may be determined. At 202, a total number of possible binary substrings that can occur in the binary data may be determined, the possible binary substrings having the given length. At 204, a normalized ratio of the number of occurrences of the given substring to the total number of the possible binary substrings may be determined. At 206, each substring having the highest normalized ratio may be selected.

In one example, a minimum substring length and a maximum substring length may be determined, and each binary substring having length between the minimum substring length and the maximum substring length may be identified. For example, the binary data may be a 100-bit string such as 1011011010100110 10101111101011101010001001110111010111101010000 11001010000111110000110000011011100111, the minimum substring length may be selected as 5, and the maximum substring length may be, selected as 15. System 100 may identify each binary substring of length between 5 and 15 that occurs in the 100-bit string. The number of occurrences of a given binary string of a given length in the 100-bit string may be determined. Additionally, the total number of possible binary substrings of the given length that may occur in the 100-bit string may be determined. A normalized ratio of the number of occurrences of the given substring to the total number of the possible binary substrings may be determined. For example, the 6-bit string "101101" occurs precisely once. There may be 95 possible binary substrings of length 6. Accordingly the normalized ratio for the string "101101" may be determined to be 1/95=0.0105263158. As another example, the 5-bit string "10101" occurs 7 times out of a possible 96 5-bit strings, as is illustrated below:

10110110101001101010111111101011
10101000100111011101011110101000
110010100001111100001100000110111001l

Accordingly, the normalized ratio for the string "10101" may be determined to be 7/96=0.0729166667. The string with the highest normalized ratio may be selected as a representative substring. In this example, the string "10101" has the highest normalized ratio of 0.0729166667.

In one example, the string with the highest normalized ratio may be utilized to tag and/or search the binary data. Also, for example, two sets of binary data may be compared based on a comparison of their respective strings with highest normalized ratios. In one example, each binary data may be associated with a plurality of binary substrings based on the normalized ratios. For example, more than one binary substring may be identified to have the highest normalized ratio. Also, for example, a threshold may be determined, and ail binary substrings having normalized ratios higher than this threshold may be selected as a summary of the binary data. Also, for example, the binary substrings may be ranked based on their respective normalized ratios, and the substrings with the highest L ratios may be selected as a summary of the binary data, where L is a natural number.

Depending on the length of the binary information in individual files and the number of files, the values of the minimum substring length and the maximum substring length and the number of representative substrings used to identify an individual binary data set may vary. For example, the substring "10101" may not be the only substring included in the summary, unless the number of classes of binary data sets is less than 32, or 2 to the $5^{th}$ power. In practice, as described herein, a large set of substrings may be identified (even the entire set of substrings that occur with length from the minimum substring length to the maximum substring length), and the individual summarization engines may be allowed to select appropriate representations of the binary substrings. These summaries may be utilized as input into the meta-algorithmic classification patterns and it may be determined as to which pattern of tokenized binary summarizers is optimal for the classification of the binary strings.

Referring to FIG. 1, at least one meta-algorithmic pattern 112 is used to summarize summaries 110(1)-110($x$) to provide a meta-summary 114. Each meta-algorithmic pattern is applied to two or more summaries to provide the meta-summary. In one example, the at least one meta-algorithmic pattern is based on one or more of the following approaches, as described herein:

(1) Sequential Try Pattern;
(2) Weighted Voting Pattern.

In other examples, a meta-algorithmic pattern may be based on another suitable approach.

The advantage of the technique described herein is that existing text summarizers may be used for binary data summarization. The binary data summarization may then be utilized for classification of binary data (even clustering of truly random data such as encrypted binary data). In the case of related binary data, this provides good classification; in the case of encrypted or otherwise random data, this provides a good hash table.

System 100 includes a plurality of classes of non-textual content 116(1)-116($y$). Class Terms 118 are based on the plurality of classes of non-textual content 116(1)-116($y$), each class term associated with each class of non-textual content, and each class vector based on class terms extracted from non-textual content in a given class. The class terms include terms, phrases and/or summary of representative or "training" content of the distinct plurality of classes of non-textual content 116(1)-116($y$). In one example, class vector 1 is associated with non-textual content class 1, class vector 2 is associated with non-textual content class 2, and class vector y is associated with non-textual content class y. As described herein, for binary data, each vector may comprise a plurality of binary substrings of the binary data that summarize the binary data.

The summarization engines and/or meta-algorithmic patterns may be utilized to reduce the tokenized non-textual content to a meta-summary. Extractor 120 generates summarization terms such as key terms and/or phrases (e.g., substrings of a binary string, key images, key audio and/or video, and so forth). In one example, extractor 120 generates a summarization vector based on the summarization terms extracted from the meta-summary of the tokenized non-textual document. The summarization vector may then be utilized as a means to classify the non-textual content.

In one example, when the non-textual content is video content, and the video content has been converted to a plurality of tokens (or descriptors), image summaries for each video segment may be processed just as if the set of descriptors were a language. The primary applications may be video classification and video tagging for indexing and search. For example, search may be performed based on similarity (find "like images") which may use both the concrete and abstract vocabularies as described herein. As another example, search may be performed based on object search (the object type/name being the query).

Non-textual content classification is the assignment of non-textual content to distinct (i.e., separate) classes of non-textual content that optimize the similarity within classes while ensuring distinction between classes. Summaries provide one means to classify non-textual content since they provide a distilled set of tokenized non-textual content that can be used for indexing and searching. For the non-textual content classification task, the summaries and meta-summaries are evaluated to determine the summarization architecture that provides the non-textual content classification that significantly matches the training (i.e., ground truth) set. The summarization architecture is then selected and recommended for deployment.

Evaluator 122 determines similarity values of the non-textual content 102 and/or the plurality of tokens 106 over each class of the plurality of classes of non-textual content 116(1)-116(y), each similarity value being indicative of a similarity between the summarization terms and each of the respective class terms. The non-textual content 102 and/or the plurality of tokens 106 may be associated with the non-textual content class 116(1)-116(y) for which the similarity between the summarization terms and the class terms is maximized.

In one example, a vector space model ("VSM") may be utilized to compute the similarity values, and in this case the similarities of the summarization vector and the class vectors. The vector space itself is an N-dimensional space in which the occurrences of each of N terms (e.g. terms in a query, substrings of a binary string) are the values plotted along each axis for each of D tokenized non-textual content. The vector $\vec{d}$ is the summarization vector of tokenized non-textual content d, and is represented by a line from the origin to the set of summarization terms for the summarization of tokenized non-textual content d, while the vector $\vec{c}$ is the class vector for class c, and is represented by a line from the origin to the set of class terms for class c. The dot product of $\vec{d}$ and $\vec{c}$, or $\vec{d} \cdot \vec{c}$, is given by:

$$\vec{d} \bullet \vec{c} = \sum_{w=1}^{N} d_w c_w \qquad \text{(Eq. 1)}$$

In one example, the similarity value between a class vector and the summarization vector may be determined based on the cosine between the class vector and the summarization vector:

$$\cos(\vec{d}, \vec{c}) = \frac{\vec{d} \bullet \vec{c}}{|\vec{d}||\vec{c}|} = \frac{\sum_{w=1}^{N} d_w c_w}{\sqrt{\sum_{w=1}^{N} d_w^2} \sqrt{\sum_{w=1}^{N} c_w^2}} \qquad \text{(Eq. 2)}$$

The cosine measure, or normalized correlation coefficient, is used for non-textual content categorization. A selector selects a class from the plurality of classes, the selection being based on the determined similarity values. In one example, the maximum cosine measure over all classes {c} is the class selected by the selector. This approach may be employed for each of the meta-algorithmic algorithms described herein in addition to each of the individual summarizers.

(1) The Sequential Try pattern may be employed to classify the non-textual content until one class is selected with a given confidence relative to the other classes. If no classification is obvious after the sequential set of tries is exhausted, the next pattern may be selected. In one example, evaluator 116 computes, for each given class i of non-textual content, a maximum similarity value of the non-textual content over all classes of non-textual content, not including the given class i. In the case where there are $N_{classes}$ of non-textual content classes, this may be described as:

$$\max\{\cos(\vec{d}, \vec{c}_j); j=1 \ldots ; j \neq i\} \qquad \text{(Eq. 3)}$$

Evaluator 116 then computes, for each given class i of non-textual content, differences between the similarity value of the non-textual content over the given class i of non-textual content and the maximum similarity value, given by:

$$\cos(\vec{d}, \vec{c}_i) - \max\{\cos(\vec{d}, \vec{c}_j); j=1 \ldots N_{classes}; j \neq i\} \qquad \text{(Eq. 4)}$$

Evaluator 116 then determines if a given computed difference of the computed differences satisfies a threshold value, and if it does, selects the class of non-textual content for which the given computed difference satisfies the threshold value. In other words, if the following holds:

$$\cos(\vec{d}, \vec{c}_i) - \max\{\cos(\vec{d}, \vec{c}); j=1 \ldots N_{classes}; j \neq i\} > T_{STC}. \qquad \text{(Eq. 5)}$$

where $T_{STC}$ is the threshold value for Sequential Try Classification, then the Sequential Try meta-algorithmic pattern terminates and the non-textual content is assigned to class i.

In one example, the threshold value $T_{STC}$ may be adjusted based on a confidence in the individual summarizer. For example, a higher confidence may generally be associated with a lower $T_{STC}$ for a classifier. In one example, the threshold value $T_{STC}$ may be adjusted based on the size of the ground truth set. For example, larger ground truth sets allow greater specificity of $T_{STC}$. In one example, the threshold value $T_{STC}$ may be adjusted based on a number of summarizers to be used in sequence. For example, more summarization engines may generally increase $T_{STC}$ for all classifiers (to avoid including too much content in the overall summarization). Generally, the larger the training data and the larger the number of summarization engines available, the better the final system performance. System performance is optimized, however, when the training data is much larger than the number of summarization engines.

Evaluator 116 may determine that each computed difference does not satisfy the threshold value, and if all the computed differences do not satisfy the threshold value, then the evaluator 116 determines that the Sequential Try meta-algorithmic pattern does not result in a clear classification. In such an instance, a (2) Weighted Voting Pattern may be selected as the meta-algorithmic pattern. Each of the multiple summarizers is tested against a ground truth (training) set of classes, and weighted by one of six methods described herein. In the Weighted Voting meta-algorithmic pattern, the output of multiple summarizers is combined and relatively weighted based on (a) the relative confidence in each engine, and (b) the relative weighting of the items (e.g., substrings of a binary string) in each summarization of the tokenized content.

For the Weighted Voting meta-algorithmic pattern, a weight determination for the individual classifiers may be based on an error rate on the training set, and the evaluator 116 selects, for deployment, the weighted voting pattern based on the weight determination. In one example, freeware, open source and simple summarizers may be combined, by applying appropriate weight determinations, to extract key tokens (e.g., key substrings from a binary string, key images, key video and/or audio segments, and so forth) from the tokenized content.

Optimal Weight Determination Approach:

In one example, with $N_{classes}$ number of classes, to which the a priori probability of assigning a sample is equal, and wherein there are $N_{classifiers}$ number of classifiers, each with its own accuracy in classification of $p_j$, where $j=1 \ldots N_{classifiers}$, the following optimal weight determination may be made:

$$W_j = \ln\left(\frac{1}{N_{classes}}\right) + \ln\left(\frac{p_j}{e_j}\right) \quad \text{(Eq. 6)}$$

where the weight of classifier j is $W_j$ and where the error term $e_j$ is given by:

$$e_j = \frac{1 - p_j}{N_{classifiers} - 1} \quad \text{(Eq. 7)}$$

Inverse-Error Proportionality Approach:

In one example, the weights may be proportional to the inverse of the error (inverse-error proportionality approach). In one example, the weights derived from the inverse-error proportionality approach may be normalized—that is, sum to 1.0, and the weight for classifier j may be given by:

$$W_j = \frac{1.0/(1.0 - p_j)}{\sum_{i=1}^{N_{classifiers}} 1.0/(1.0 - p_i)} \quad \text{(Eq. 8)}$$

Proportionality to Accuracy Squared Approach:

In one example, the weight determinations may be based on proportionality to accuracy raised to the second power (accuracy-squared) approach. In one example, the associated weights may be described by the following equation:

$$W_j = \frac{p_j^2}{\sum_{i=1}^{N_{classifiers}} p_i^2} \quad \text{(Eq. 9)}$$

The inverse-error proportionality approach may favor the relatively more accurate classifiers in comparison to the optimal weight determination approach. The proportionality to accuracy-squared approach may favor the relatively less accurate classifiers in comparison to the optimal weight determination approach. Accordingly, a hybrid method comprising the inverse-error proportionality approach and the proportionality to accuracy-squared approach may be utilized.

Hybrid Weight Determination Approach:

In the hybrid weight determination approach, a mean weighting of the inverse-error proportionality approach and the proportionality to accuracy-squared approach may be utilized to provide a performance closer to the "optimal" weight determination. In one example, the hybrid weight determination approach may be given by the following equation:

$$W_j = \lambda_1 \frac{1.0/(1.0 - p_j)}{\sum_{i=1}^{N_{classifiers}} 1.0/(1.0 - p_i)} + \lambda_2 \frac{p_j^2}{\sum_{i=1}^{N_{classifiers}} p_i^2} \quad \text{(Eq. 10)}$$

where $\Delta_1 + \Delta_2 = 1.0$. Varying the coefficients $\lambda_1$ and $\lambda_2$ may allow the system to be adjusted for different factors, including accuracy, robustness, lack of false positives for a given class, and so forth.

Inverse of the Square Root of the Error Approach:

In one example, the weight determinations may be based on an inverse of the square root of the error. The behavior of this weighting approach is similar to the hybrid weight determination approach, as well as the optimal weight determination approach. In one example, the weights may be defined as:

$$W_j = \frac{1.0/\sqrt{1.0 - p_j}}{\sum_{i=1}^{N_{classifiers}} 1.0/\sqrt{1.0 - p_i}} \quad \text{(Eq. 11)}$$

After the individual weights are determined, classification assignment may be given to the class with the highest weight. In one example, evaluator 116 performs the classification assignment. In one example, the highest weight may be determined as:

$$Classification = \max_i \sum_{j=1}^{N_C} ClassifierWeight_j * ClassWeight_{i,j} \quad \text{(Eq. 12)}$$

where $N_C$ is the number of classifiers, i is the index for the non-textual content classes, j is the index for the classifier, $ClassWeight_{i,j}$ is the confidence each particular classifier j has for the class i, and $ClassifierWeight_j$ is the weight of classifier j based on the weight determination approaches described herein.

An example classification assignment is illustrated in Table 1. The example illustrates a situation with two classifiers A and B, and four classes $C_1$, $C_2$, $C_3$, and $C_4$. The confidence in classifier A, $ClassifierWeight_A$, may be 0.6 and the confidence in classifier B, $ClassifierWeight_B$, may be 0.4. Such confidence may be obtained based on the weight determination approaches described herein. In this example, classifier A assigns weights $ClassWeight_{1,A}=0.3$, $ClassWeight_{2,A}=0.4$, $ClassWeight_{3,A}=0.1$, and $ClassWeight_{4,A}=0.2$ to each of classes $C_1$, $C_2$, $C_3$, and $C_4$, respectively. Also, for example, classifier B assigns weights $ClassWeight_{1,B}=0.5$, $ClassWeight_{2,B}=0.3$, $ClassWeight_{3,B}=0.2$, and $ClassWeight_{4,B}=0.0$ to each of classes $C_1$, $C_2$, $C_3$, and $C_4$, respectively. Then the weight assignment for each class may be obtained as illustrated in Table 1.

TABLE 1

| | Classification Assignment based on Weight Determination | | | | |
|---|---|---|---|---|---|
| | $ClassifierWeight_j$, j = A, | $ClassWeight_{i,j}$, j = A, B, i = 1, 2, 3, 4. | | | |
| Classifier | B | $C_1$ | $C_2$ | $C_3$ | $C_4$ |
| A | $ClassifierWeight_A = 0.6$ | 0.3 | 0.4 | 0.1 | 0.2 |
| B | $ClassifierWeight_B = 0.4$ | 0.5 | 0.3 | 0.2 | 0.0 |

TABLE 1-continued

Classification Assignment based on Weight Determination

| | ClassifierWeight$_j$, j = A, | ClassWeight$_{i,j}$, j = A, B, i = 1, 2, 3, 4. | | | |
|---|---|---|---|---|---|
| Classifier | B | C$_1$ | C$_2$ | C$_3$ | C$_4$ |
| Weight Assignment for each Class i = $\sum_{j=A,B}$ ClassifierWeight$_j$ * ClassWeight$_{i,j}$ | | (0.6)*(0.3) + (0.4)*(0.6) = 0.38 | (0.6)*(0.4) + (0.4)*(0.3) = 0.36 | (0.6)*(0.1) + (0.4)*(0.2) = 0.14 | (0.6)*(0.2) + (0.4)*(0.0) = 0.12 |

Accordingly, $$\max_i \sum_{j=1}^{N_C} ClassifierWeight_j * ClassWeight_{i,j} = \quad \text{(Eq. 13)}$$

$$\max(0.38, 0.36, 0.14, 0.12) = 0.38.$$

In this example, the maximum weight assignment of 0.38 corresponds to class $C_1$. Based on such a determination, the evaluator 116 selects class $C_1$ for classification.

Figure 3:
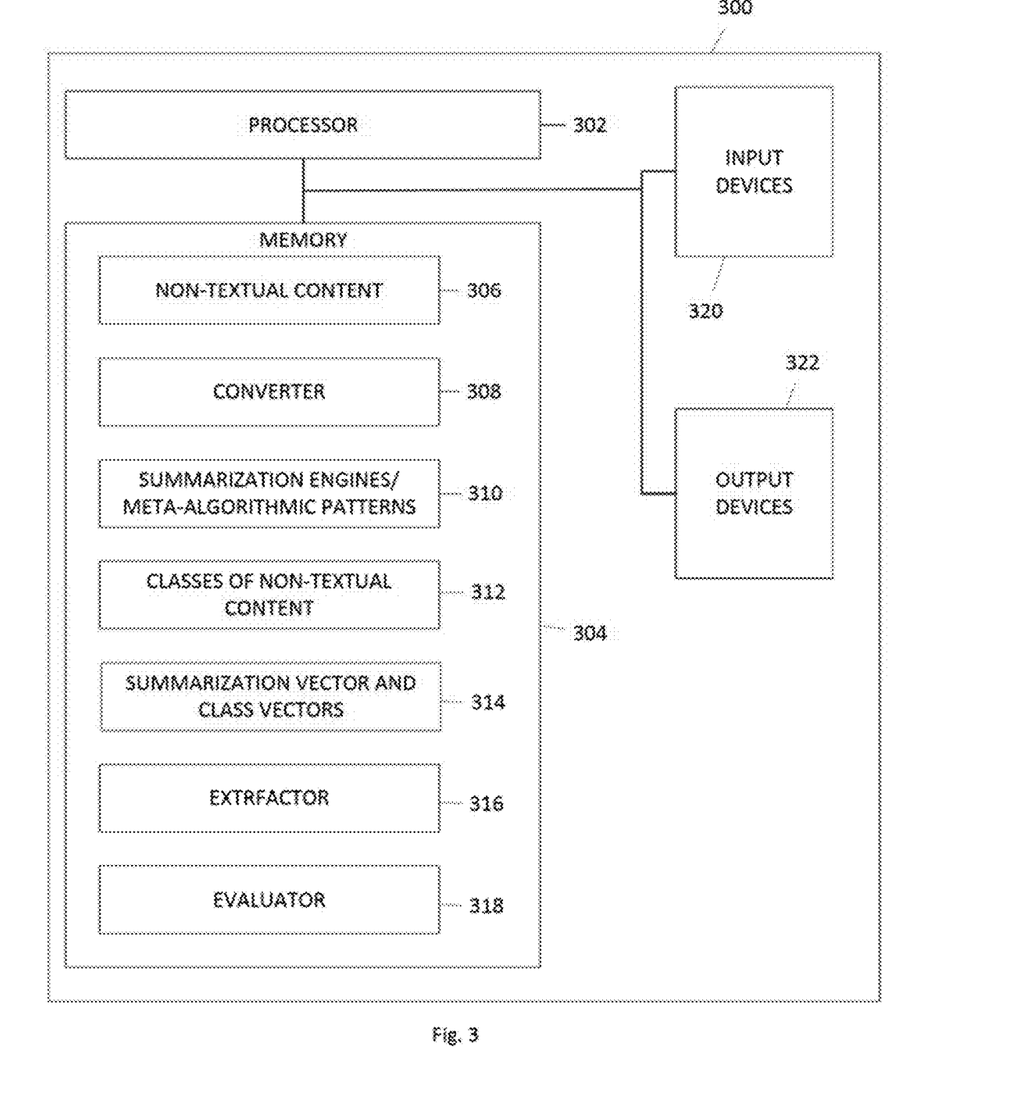
FIG. 3 is a block diagram illustrating one example of a processing system for implementing the system for functional summarization of non-textual content based on a meta-algorithmic pattern.

FIG. 3 is a block diagram illustrating one example of a processing system 300 for implementing the system 100 for functional summarization of non-textual content based on a meta-algorithmic pattern. Processing system 300 includes a processor 302, a memory 304, input devices 318, and output devices 320. Processor 302, memory 304, input devices 318, and output devices 320 are coupled to each other through communication link (e.g., a bus).

Processor 302 includes a Central Processing Unit (CPU) or another suitable processor. In one example, memory 304 stores machine readable instructions executed by processor 302 for operating processing system 300. Memory 304 includes any suitable combination of volatile and/or non-volatile memory, such as combinations of Random Access Memory (RAM), Read-Only Memory (ROM), flash memory, and/or other suitable memory.

Memory 304 stores non-textual content 306 for processing by processing system 300. In one example, memory 304 stores a plurality of classes of non-textual content for processing by processing system 300. Memory 304 also stores instructions to be executed by processor 302 including instructions for a converter 308, summarization engines and/or meta-algorithmic patterns 310, an extractor 316, and an evaluator 318. In one example, memory 304 also stores the summarization vector and class vectors 314. In one example, converter 308, summarization engines and/or meta-algorithmic patterns 310, extractor 316 and evaluator 318, include converter 104, summarization engines 108, the at least one meta-algorithmic pattern 112, extractor 120, and evaluator 122, respectively, as previously described and illustrated with reference to FIG. 1.

In one example, processor 302 executes instructions of converter 308 to convert non-textual content 306 to provide a plurality of tokens. Processor 302 executes instructions of a plurality of summarization engines and/or meta-algorithmic patterns 310 to summarize the non-textual content 306 to provide a meta-summary. In one example, the plurality of summarization engines and/or meta-algorithmic patterns 310 may identify the substrings of highest normalized ratios in binary data. In one example, the plurality of summarization engines and/or meta-algorithmic patterns 310 may include a sequential try pattern, followed by a weighted voting pattern, as described herein. In one example, processor 302 executes instructions of an extractor 316 to generate at least one summarization term from the meta-summary of the non-textual content 306. In one example, a summarization vector 314 may be generated based on the at least one summarization term extracted from the meta-summary. In one example, processor 302 executes instructions of extractor 316 to generate at least one class term for each given class of a plurality of classes of non-textual content 312, the at least one class term extracted from the non-textual content in the given class. In one example, a class vector 314 may be generated for each given class of a plurality of classes of non-textual content 312, the class vector 314 being based on the at least one class term extracted from the non-textual content in the given class. Processor 302 executes instructions of evaluator 318 to determine the similarity values of the non-textual content 306 over each class of the plurality of classes of non-textual content 312, each similarity value indicative of a similarity between the at least one summarization term and the at least one class term for each given class. In one example, the similarity values may be based on the cosine similarity between the summarization vector and each class vector. In one example, processor 302 executes instructions, of a selector to select a class of the plurality of classes, the selection based on the determined similarity values. In one example, processor 302 executes instructions of a selector to associate, in a database, the non-textual content with the selected class of non-textual content.

In one example, the non-textual content may be healthcare data of an individual, and the plurality of classes of non-textual content is a plurality of classes of healthcare data of individuals. The processor 302 executes instructions of the selector to select a class of the plurality of classes of healthcare data of individuals, the selection based on the determined similarity values. In one example, processor 302 executes instructions of the selector to associate, in a database, the healthcare data of the individual with the selected class of healthcare data of individuals. As described herein, publicly available healthcare data may be converted to binary data and summarized, and the plurality of summarization engines and/or meta-algorithmic patterns 310 for summarization may be tuned to best classify the individual (e.g. for clinical studies, healthcare provider recommendation, and so forth).

Input devices 320 include a keyboard, mouse, data ports, and/or other suitable devices for inputting information into processing system 300. In one example, input devices 320 are used to input feedback from users for evaluating non-textual content, an associated meta-summary, an associated class of individuals, and/or an associated class of non-textual content, for search queries. Output devices 322 include a monitor, speakers, data ports, and/or other suitable devices for outputting information from processing system 300. In one example, output devices 322 are used to output summaries and meta-summaries to users and to recommend a classification for the non-textual content, and/or for individuals, in one example, a classification query directed at a non-textual content is received via input devices 320. The processor 302 retrieves, from the database, a class associated with the text non-textual content, and provides such classification via output devices 322.

Figure 4:
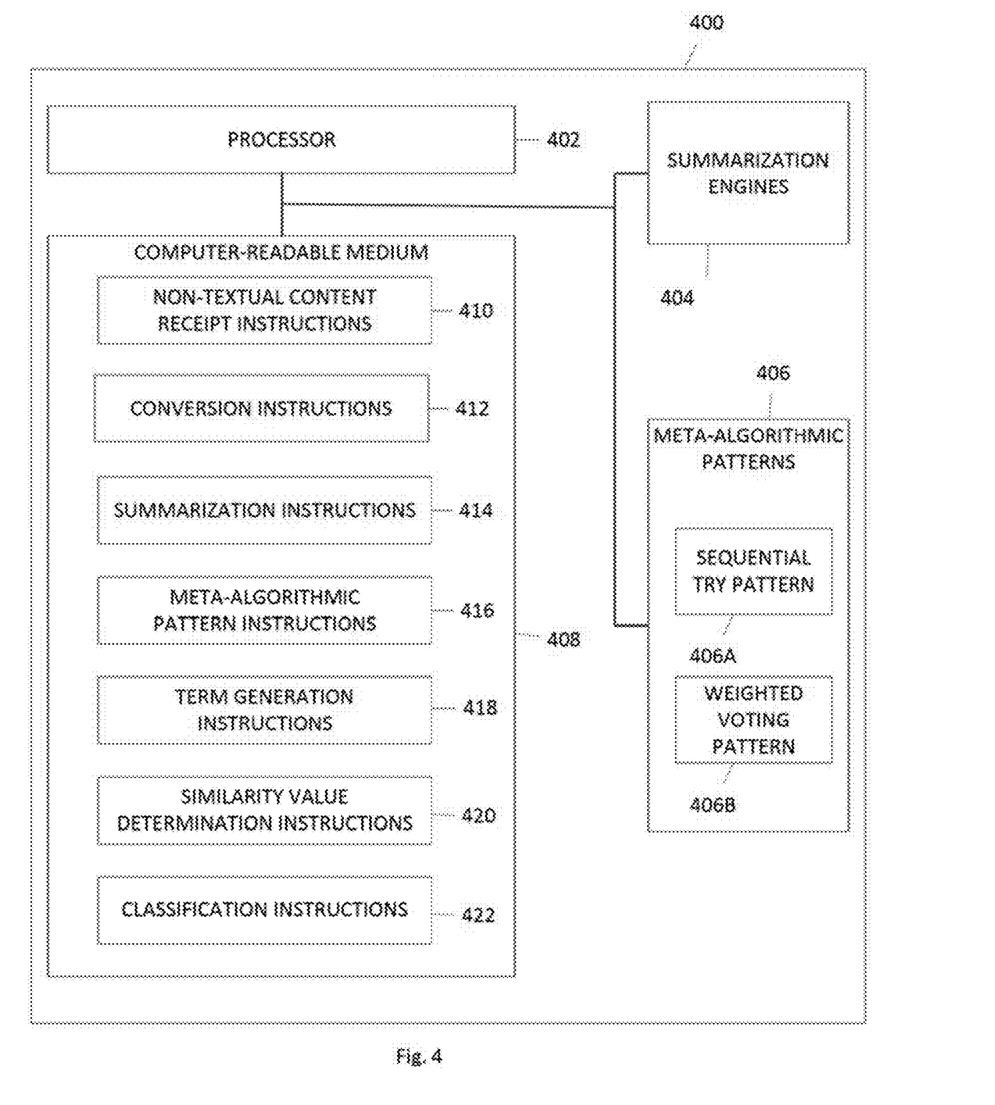
FIG. 4 is a block diagram illustrating one example of a computer readable medium for functional summarization of non-textual content based on a meta-algorithmic pattern.

FIG. 4 is a block diagram illustrating one example of a computer readable medium for functional summarization of non-textual content based on a meta-algorithmic pattern. Processing system 400 includes a processor 402, a computer readable medium 408, a plurality of summarization engines 404, and at least one meta-algorithmic pattern 406. In one example, the at least one meta-algorithmic pattern 406 includes the Sequential Try Pattern 406A and the Weighted Voting Pattern 406B. Processor 402, computer readable medium 408, the plurality of summarization engines 404, and the at least one meta-algorithmic pattern 406 are coupled to each other through communication link (e.g., a bus).

Processor 402 executes instructions included in the computer readable medium 408. Computer readable medium 408 includes non-textual content receipt instructions 410 to receive non-textual content. Computer readable medium 408 includes conversion instructions 412 of a converter to convert the non-textual content into a plurality of tokens. Computer readable medium 408 includes summarization instructions 414 of a plurality of summarization engines 404 to summarize the received non-textual content and/or converted plurality of tokens to provide summaries. Computer readable medium 408 includes meta-algorithmic pattern instructions 416 of at least one meta-algorithmic pattern 406 to summarize the summaries to provide a meta-summary. Computer readable medium 408 includes term generation instructions 418 to generate class terms and summarization terms. In one example, term generation instructions 418 include instructions to generate a summarization vector based on summarization terms extracted from the meta-summary. In one example, computer readable medium 408 includes term generation instructions 418 to generate a class vector for each given class of a plurality of classes of non-textual content, the class vector being based on class terms extracted from non-textual content in the given class. In one example, the non-textual content is the healthcare data of an individual, and the plurality of classes of non-textual content is a plurality of classes of healthcare data of individuals. In one example, computer readable medium 408 includes term generation instructions 418 to generate a class vector for each given class of a plurality of classes of healthcare data of individuals, the class vector being based on class terms extracted from individual healthcare data in the given class. As described herein, the class vector may comprise binary substrings extracted from the healthcare data for a given class of individuals.

Computer readable medium 408 includes similarity value determination instructions 420 of evaluator to determine similarity values of the non-textual content over each given class of the plurality of classes of non-textual content, each similarity value indicative of a similarity between the at least one summarization term and the at least one class term for each given class. Computer readable medium 408 includes classification instructions 422 of selector to select a class of the plurality of classes of non-textual content and/or individuals, the selecting based on the determined similarity values. In one example, computer readable medium 408 includes instructions to associate the selected class with the non-textual content.

Figure 5:
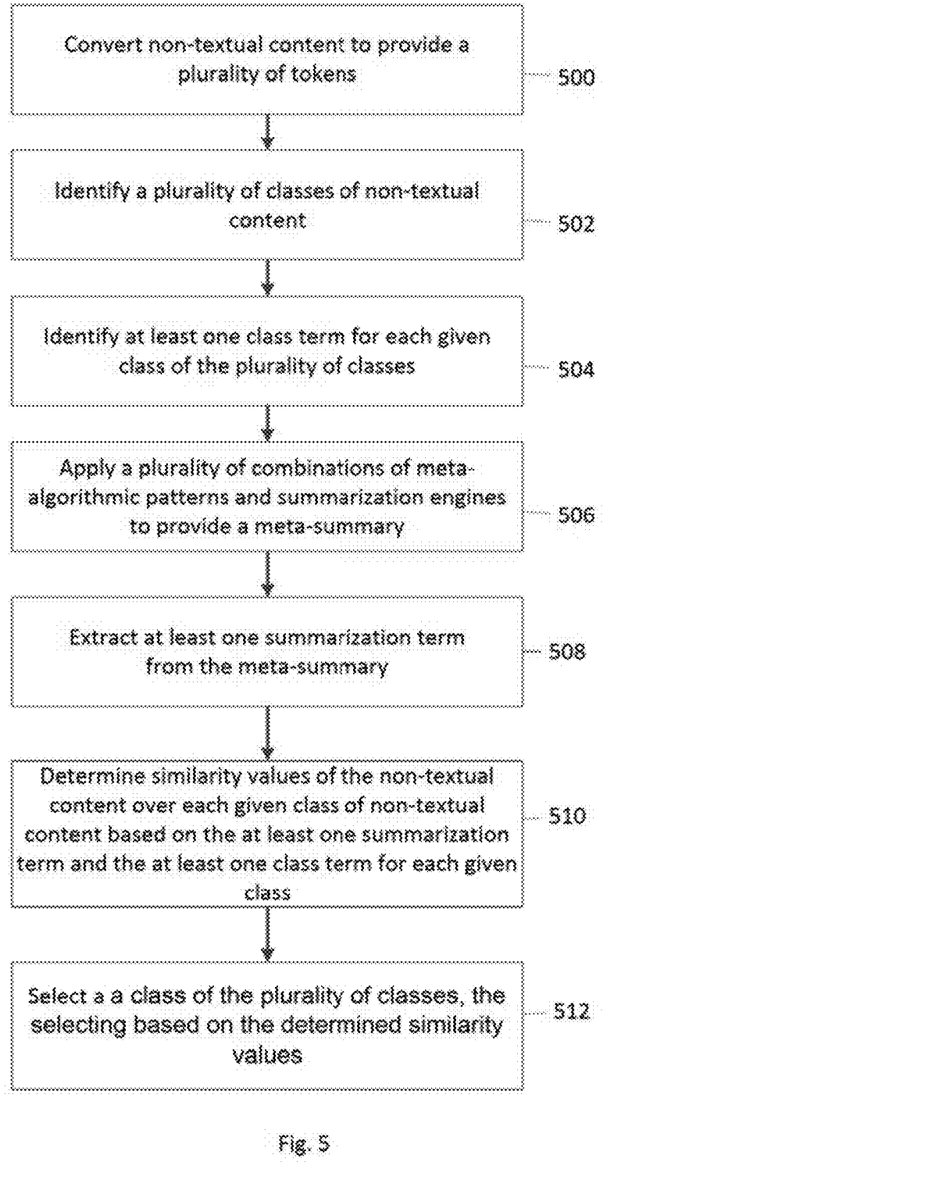
FIG. 5 is a flow diagram illustrating one example of a method for functional summarization of non-textual content based on a meta-algorithmic pattern.

FIG. 5 is a flow diagram illustrating one example of method for functional summarization of non-textual content based on a meta-algorithmic pattern. At 500, non-textual content is converted to provide a plurality of tokens. At 502, a plurality of classes of non-textual content is identified. At, 504, at least one class term is identified for each given class of the plurality of classes of non-textual content. At 506, a plurality of combinations of meta-algorithmic patterns and summarization engines are applied to provide a meta-summary of the plurality of tokens. At 508, at least one summarization term is extracted from the meta-summary. At 510, similarity values of the non-textual content over each given class of the plurality of classes of non-textual content are determined, each similarity value indicative of a similarity between the at least one summarization term and the at least one class term for each given class. At 512, a class of the plurality of classes is selected, the selecting based on the determined similarity values.

In one example, the non-textual content may be at least one of an image, audio content, video content, binary data, genetic data, and healthcare data.

In one example, the method may include associating, in a database, the non-textual content with the selected class of non-textual content.

In one example, the non-textual content may be the binary data, the plurality of tokens may include binary substrings, and the method may further include identifying a substring with a high frequency in the binary data.

In one example, the meta-algorithmic pattern may be a sequential try pattern, and the method may include determining that one of the similarity values satisfies a threshold value, selecting a given class of the plurality of classes for which the determined similarity value satisfies the threshold value, and associating the non-textual content with the given class. In one example, the method may further include determining that each of the similarity values fails to satisfy the threshold value, and selecting a weighted voting pattern as the meta-algorithmic pattern.

Examples of the disclosure provide a generalized system for using multiple summaries and meta-algorithms to optimize a text and/or non-textual-related intelligence generating or machine intelligence system. The generalized system provides a pattern-based, automatable approach to non-textual content classification based on summarization that may learn and improve over time, and is not fixed on a single technology or machine learning approach. In this way, the content used to represent a larger body of non-textual content, suitable to a wide range of applications, may be classified.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A system comprising:
a processor; and
a non-transitory computer readable medium storing instructions that are executed by the processor to:

convert non-textual content into binary data and tokenize the binary data associated with the non-textual content into a plurality of tokens;

receive, via each summarization engine of a plurality of summarization engines, the plurality of tokens to provide a summary of the non-textual content, wherein the summary of the non-textual content comprises a binary substring;

apply each meta algorithmic pattern of at least one meta algorithmic pattern to at least two summaries to provide a meta-summary of the non-textual content using the at least two summaries;

identify at least one class term for each given class of a plurality of classes of non-textual content, the at least one class term extracted from non-textual content in the given class, wherein the at least one class term comprises the binary substring having a normalized ratio higher than a threshold;

extract at least one summarization term from the meta-summary;

determine similarity values of the non-textual content over each given class of the plurality of classes of non-textual content, each similarity value indicative of a similarity between the at least one summarization term and the at least one class term for each given class; and select a class of the plurality of classes for the non-textual content based on the similarity values that are determined.

2. The system of claim 1, wherein the non-textual content is the genetic data, and the genetic data is converted into the binary data.

3. The system of claim 1, wherein the non-textual content is the healthcare data of an individual, and the plurality of classes of non-textual content is a plurality of classes of healthcare data of individuals.

4. A method to classify non-textual content based on a meta-algorithm pattern, the method comprising:

converting the non-textual content into binary data and tokenizing the binary data associated with the non-textual content to provide a plurality of tokens;

identifying a plurality of classes of documents via a processor;

identifying at least one class term for each given class of the plurality of classes of non-textual content, the at least one class term extracted from content in the given class, wherein the at least one class term comprises a binary substring having a normalized ratio higher than a threshold;

applying, to the plurality of tokens, a plurality of combinations of meta-algorithmic patterns and summarization engines, wherein each summarization engine provides a summary of the plurality of tokens, wherein the summary of the non-textual content comprises the binary substring, and each meta-algorithmic pattern is applied to at least two summaries to provide, via the processor, a meta-summary; and extracting at least one summarization term from the meta-summary; determining, via the processing system, similarity values of the non-textual content over each given class of the plurality of classes of non-textual content, each similarity value indicative of a similarity between the at least one summarization term and the at least one class term for each given class; and selecting a class of the plurality of classes for the non-textual content based on the similarity values that are determined.

5. The method of claim 4, wherein identifying the substring with the high frequency comprises:

determining, for each given substring of a given length, a number of occurrences of the given substring in the binary data;

determining a total number of possible binary substrings that can occur in the binary data, the possible binary substrings having the given length;

determining the normalized ratio of the number of occurrences of the given substring to the total number of the possible binary substrings; and selecting each substring having a highest normalized ratio.

6. The method of claim 4, wherein the meta-algorithmic pattern is a sequential try pattern, and further including:

determining that one of the similarity values satisfies a similarity threshold value;

selecting a given class of the plurality of classes for which the determined similarity value satisfies the threshold value; and associating the non-textual content with the given class.

7. The method of claim 6, further including:

determining that each of the similarity values fails to satisfy the similarity threshold value; and selecting a weighted voting pattern as the meta-algorithmic pattern.

8. A non-transitory computer readable medium comprising executable instructions to:

receive a non-textual content via a processor;

convert the non-textual content into binary data and tokenizing the binary data associated with the non-textual content to provide a plurality of tokens;

apply a plurality of combinations of meta-algorithmic patterns and summarization engines to the plurality of tokens, wherein each summarization engine provides a summary of the plurality of tokens, wherein the summary of the non-textual content comprises a binary substring, and each meta-algorithmic pattern is applied to at least two summaries to provide, via the processor, a meta-summary;

extract at least one summarization term from the meta-summary; generate at least one class term for each given class of a plurality of classes of non-textual content, the at least one class term extracted from non-textual content in the given class, wherein the at least one class term comprises the binary substring having a normalized ratio higher than a threshold;

determine similarity values of the non-textual content over each given class of the plurality of classes of non-textual content, each similarity value indicative of a similarity between the at least one summarization term and the at least one class term for each given class; and select a class of the plurality of classes for the non-textual content based on the similarity values that are determined.

* * * * *

UNITED STATES PATENT AND TRADEMARK OFFICE
CERTIFICATE OF CORRECTION

PATENT NO. : 10,394,867 B2  
APPLICATION NO. : 15/317940  
DATED : August 27, 2019  
INVENTOR(S) : Steven J Simske et al.

Page 1 of 1

It is certified that error appears in the above-identified patent and that said Letters Patent is hereby corrected as shown below:

In the Drawings

In sheet 3 of 5, reference numeral 316, Line 1, delete "EXTRFACTOR" and insert -- EXTRACTOR --, therefor.

In sheet 5 of 5, reference numeral 512, Line 1, delete "a a" and insert -- a --, therefor.

Signed and Sealed this
Thirty-first Day of December, 2019

Andrei Iancu
*Director of the United States Patent and Trademark Office*